US012797880B2

(12) United States Patent
Greiner-Perth et al.

(10) Patent No.: US 12,797,880 B2
(45) Date of Patent: Nov. 17, 2026

(54) DISPENSING HEAD FOR PHARMACEUTICAL OR COSMETIC LIQUIDS

(71) Applicant: Aptar Radolfzell GmbH, Radolfzell (DE)

(72) Inventors: Jürgen Greiner-Perth, Gottmadingen (DE); Stefan Ritsche, Eigeltingen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 79 days.

(21) Appl. No.: 18/862,209

(22) PCT Filed: Feb. 9, 2023

(86) PCT No.: PCT/EP2023/053250
§ 371 (c)(1),
(2) Date: Nov. 1, 2024

(87) PCT Pub. No.: WO2023/213455
PCT Pub. Date: Nov. 9, 2023

(65) Prior Publication Data
US 2025/0339867 A1 Nov. 6, 2025

(30) Foreign Application Priority Data
May 3, 2022 (EP) .................................... 22171432

(51) Int. Cl.
*B05B 11/00* (2023.01)
*A61M 11/00* (2006.01)
*A61M 15/08* (2006.01)

(52) U.S. Cl.
CPC ......... *B05B 11/007* (2013.01); *A61M 11/007* (2014.02); *A61M 15/08* (2013.01)

(58) Field of Classification Search
CPC ............... B05B 11/007; B05B 11/1014; B05B 11/1012; B05B 11/0062; B05B 11/10;
(Continued)

(56) References Cited

U.S. PATENT DOCUMENTS 2,824,672 A 2/1958 Wersching
5,673,824 A 10/1997 Evans
(Continued)

FOREIGN PATENT DOCUMENTS

EP 0250965 B1 1/1988
WO 2006122983 A1 11/2006

OTHER PUBLICATIONS

International Search Report, with English translation, issued in corresponding International Application No. PCT/EP2023/053250, date of mailing May 19, 2023 (9 pages).
(Continued)

*Primary Examiner* — David J Walczak
(74) *Attorney, Agent, or Firm* — FLYNN THIEL, P.C.

(57) ABSTRACT

A dispensing head for pharmaceutical or cosmetic liquids, including a base unit for attaching to a liquid reservoir and a dispensing unit having an applicator housing penetrated by a dispensing opening. The dispensing unit is displaceable, counter to the force of a restoring spring, relative to the base unit. Further, a pump device of the dispensing head is activatable by movement of the dispensing unit relative to the base unit and conveys liquid from the liquid reservoir to the dispensing opening. The restoring spring is configured as a plastics-material spring.

25 Claims, 8 Drawing Sheets

(58) Field of Classification Search
CPC ... A61M 11/007; A61M 15/08; A61M 11/006
USPC .................. 222/372, 383.1, 383.3, 385, 387
See application file for complete search history.

(56) References Cited

U.S. PATENT DOCUMENTS

| | | | | |
|---|---|---|---|---|
| 6,398,074 | B1 * | 6/2002 | Bruna .................. | B05B 11/062 222/386 |
| 6,672,486 | B2 | 1/2004 | Santagiuliana | |
| 7,246,723 | B2 | 7/2007 | Santagiuliana | |
| 2003/0075567 | A1 | 4/2003 | Santagiuliana | |
| 2005/0023295 | A1 * | 2/2005 | Tempfli ................ | B05B 11/061 222/321.9 |
| 2005/0165368 | A1 | 7/2005 | Py et al. | |

OTHER PUBLICATIONS

Written Opinion of International Searching Authority, issued in corresponding International Application No. PCT/EP2023/053250, date of mailing May 19, 2023 (6 pages).

* cited by examiner

DISPENSING HEAD FOR PHARMACEUTICAL OR COSMETIC LIQUIDS

TECHNICAL FIELD

The invention relates to a liquid dispenser, and to a dispensing head provided therefor, for pharmaceutical and cosmetic liquids. The dispensing head includes a base unit for attaching to a liquid reservoir, as well as a dispensing unit which is displaceable relative to the base unit. The dispensing unit has a dispensing opening by way of which liquid can be dispensed. The dispensing head has a pump device which can be activated by depressing the dispensing unit in the direction of the base unit, and by means of which liquid that has previously been inducted from the liquid dispenser into a pump chamber of the pump device can be dispensed.

After depressing the dispensing unit for the purpose of dispensing the liquid, the dispensing unit in the course of a restoring movement returns to its initial position in which said dispensing unit is spaced apart from the base unit. In the process, liquid from the liquid reservoir is inducted into the pump chamber, said liquid being at least partially dispensed when the dispensing unit is depressed the next time. The dispensing head has a restoring spring which is tensioned when depressing the dispensing unit, and subsequently causes the restoring movement.

BACKGROUND AND SUMMARY

Liquid dispensers of the generic type are usually designed as single-use dispensers. They are disposed of once the liquid in the liquid reservoir has been consumed.

OBJECT AND ACHIEVEMENT

One object is to design a liquid dispenser of the type described above, or its dispensing head, in such a manner that a high degree of recyclability is achieved.

Proposed for this purpose is a dispensing head for pharmaceutical or cosmetic liquids, as well as a non-filled or filled liquid dispenser which comprises a liquid reservoir as well as a dispensing head of the type mentioned.

The dispensing head, in the manner described above, comprises a base unit which is connected to the liquid reservoir, in particular by means of a threaded connection or snap-fit connection. An integral connection of the base unit and the liquid reservoir is also possible.

The dispensing unit of the dispensing head is displaceable, preferably linearly displaceable, relative to this base unit, in particular in a direction which is identical to a central axis of the base unit and/or of the liquid reservoir. The dispensing unit is manually impinged with a force relative to the base unit. The user preferably encompasses the base unit or the liquid reservoir, and depresses the dispensing unit by means of the index finger and/or middle finger.

The pump device is disposed between the base unit and the dispensing unit in such a manner that said pump device is activated by the relative displacement of the base unit and the dispensing unit. The pump device preferably has a pump chamber. An inlet duct, which is provided with an inlet valve, connects the pump chamber to the liquid reservoir. An outlet duct, which is provided with an outlet valve, connects the pump chamber to the dispensing opening which penetrates an applicator housing of the dispensing unit. The inlet valve is closed and the outlet valve is opened when depressing the dispensing unit, so that the liquid exits. The outlet valve closes and the inlet valve opens in the subsequent return stroke, so that the pump chamber, which is enlarged in the process, inducts liquid from the liquid reservoir, preferably by means of a riser which protrudes into the liquid reservoir, or from a collapsing bag within the liquid reservoir.

The dispensing head is preferably easy to recycle. In particular, it can be composed completely or almost completely (>99%) of plastics material, preferably of plastics materials that can be processed in a common recycling process. According to the invention, the restoring spring which acts between the base unit and the dispensing unit is also designed as a plastics-material spring.

The restoring spring can in particular be a bellows spring, thus a bellows which is closed in an encircling manner and by way of its two ends bears on faces of the dispensing unit and of the base unit. When the dispensing unit is depressed, the bellows spring is axially compressed and elastically tensioned in the process. The bellows spring relaxes in the absence of the depressing force, thus pushing the dispensing unit away from the base unit again. TPE (thermoplastic elastomer) is a preferred material for the bellows spring.

In principle, it is possible to dispose the restoring spring of plastics material within an interior space surrounded by the dispensing unit and the base unit, so that said restoring spring is not visible from the outside. If this approach is chosen, dispensing heads which were originally provided for receiving metallic coil springs can instead be equipped with plastics-material bellows springs that are inserted into the same receptacle space into which metallic coil springs are inserted in other variants. This permits many, or even all other, parts between two variants of the dispensing head with a metal spring and a plastics-material spring to be of identical design.

However, it is preferably provided that the restoring spring is attached to an external side of the dispensing unit and is therefore visible during regular operation. As a result, the requirement of having to provide the interior space defined by the base unit and the dispensing unit to be sufficiently large for a bellows spring in the relaxed state and in the compressed state is avoided.

In particular, the restoring spring of plastics material is disposed in such a way that it encases external faces of the base unit and of the dispensing unit at least in portions. In such a case, it is also considered advantageous when the dispensing unit and the base unit have a spring receptacle space in an interior space which is conjointly enclosed by these elements, which spring receptacle space is designed to receive a coil spring, so that a coil spring of metal may also be used instead of the restoring spring of plastics material.

However, in the design with plastics-material springs, there are preferably no coil springs disposed in the spring receptacle space, and the spring receptacle space remains empty. The latter thus serves only for receiving a metallic coil spring if the dispensing unit of largely identical construction and the base unit of largely identical construction are designed without a plastics-material spring in another variant. Annular contact faces for the coil spring are preferably provided in each case on the base unit and the dispensing unit, wherein the annular contact faces on the inside and/or outside are preferably flanked by guide faces.

A variant in which an internal metallic coil spring as well as an external plastics-material spring, in particular a bellows spring, are provided in such a way that an increased common spring force is achieved is also conceivable.

If the plastics-material spring is provided on the external side of the dispensing head, an upper side of the base unit thus preferably provides a force-introduction face.

The opposite force-introduction face on the side of the dispensing unit is preferably formed by a finger rest. This finger rest is provided on the dispensing unit for the purpose of manually impinging the dispensing unit with a force in the direction of the base unit. This is particularly preferably a finger rest with an annular shape which surrounds the applicator housing of the dispensing unit.

The finger rest can in particular have a width which is consistent in an encircling manner, or include two mutually opposite activation tabs for bringing the index finger and middle finger to bear.

In the case of such a design with activation tabs, the finger rest thus externally has an non-circular shape. The finger rest can in particular have two bearing regions for two fingers on mutually opposite sides of the applicator housing. Such a design enables the avoidance of rolling of the dispenser during handling in recycling, in particular on a conveyor belt.

The restoring spring preferably acts on this finger rest, and for this purpose bears in particular on a lower side of the finger rest, or is fastened there.

The finger rest can be integrally molded on the applicator housing. As opposed thereto, it is however preferable that this is a separate component which is fastened to the applicator housing, in particular by means of a snap-fit connection. This permits the use of different finger rests for versions of the dispensing head with and without an external plastics-material spring.

Furthermore, the finger rest can be designed to be integral to the plastics-material spring. A potential construction mode herein provides that the part forming the finger rest and the part forming the plastics-material spring are composed of a uniform, identical material, for example a TPE plastics material. The material herein is primarily conceived by way of the desired deformation characteristic of the plastics-material spring. The part forming the finger rest is preferably reinforced by a greater wall thickness than the spring part and/or by additional ribbing in such a way that it tends to deform only to an acceptable degree.

However, an integral design of the finger rest and the plastics-material spring can also be formed by a materially integral connection of two different plastics materials. A more rigid part herein forms at least part of the upper side of the finger rest, while a more elastic part forms the spring part of the integral component. Additionally, the rigid part can be designed to be integral to the applicator housing, or else be designed as a separate part. A materially integral connection is preferably produced by a multi-component injection-molding process, wherein a first plastics material is initially incorporated into an expandable injection-molding cavity, and a second plastics material is subsequently incorporated upon expansion of the cavity. The plastics materials form an inherent and air-tight connection in a boundary zone. In an integral design with a plurality of plastics materials it can be advantageous for the boundary zone to be shaped in such a way that the parts of different plastics materials, in addition to the materially integral fit, are also connected to one another in a form-fitting manner by means of undercuts.

The integral design of the finger rest with the plastics-material spring simplifies assembling because the spring is simultaneously also moved to its target position by attaching the finger rest to the application housing. However, the same can also be achieved with a two-piece design in which the finger rest and the plastics-material spring are separately produced parts which are already connected to one another in a force-fitting or form-fitting manner, for example by a clamping connection, prior to being attached to the applicator housing.

If the finger rest and the restoring spring are designed as separate components it is advantageous for a centering geometry to be provided on the finger rest, and in particular on the lower side of the latter, said centering geometry guiding a force-introduction face of the restoring spring from the inside and/or outside and preferably also serving to couple the restoring spring and the finger rest in a force-fitting or form-fitting manner. If the finger rest and the restoring spring are designed as separate parts, and if the restoring spring is designed as a bellows spring, it is advantageous when that side of the bellows spring that bears on the finger rest has a collar which acts toward the outside or preferably toward the inside and protrudes beyond the bellows segments toward the outside or inside, respectively, by at least 5%, preferably by at least 10%, in terms of the diameter. This collar facilitates demolding during production of the bellows spring.

Preferably the finger rest, or else another part of the dispensing unit or of the base unit, depending on the construction mode, may be the support of the restoring spring. This means that the restoring spring is fixedly connected to this component acting as the support. Clamping connections as well as integral connections, in particular materially integral connections, in which the component acting as the support and the restoring spring are composed of different materials but by multi-component injection-molding are non-releasably and inherently connected to one another, may be considered here.

When the support is assembled, the restoring spring is also moved to its target position as a result. This facilitates assembling of the restoring spring. The restoring spring is not fixedly assembled to components other than the support component, but comes into contact with other components only during assembling or when activated.

In comparison to a metallic restoring spring, the use of a plastics-material spring, in particular a bellows spring, leads to a restoring force which tends to be weaker. Therefore, the dispensing unit does not reach the non-activated initial position with the same degree of reliability as in the case of a metallic restoring spring. In order to nevertheless guarantee a reproducible dispensed quantity despite the resultant potentially reduced length of stroke, it can be provided that the pump device is designed in such a manner and/or coupled to the dispensing unit in such a manner that, proceeding from the initial position, a displacement of the dispensing unit in the direction of the activated terminal position does not cause any liquid dispensation over a partial length of stroke. Proceeding from the terminal position, the initial activation therefore at first does not lead to any dispensation, preferably in that a return flow of liquid from the pump chamber into the liquid reservoir is at first still possible. During activation, the return flow is only shut off after a short partial length of stroke, preferably after at least 3% of the total length of stroke, in particular after at least 6% of the total length of stroke. The pump chamber is isolated, and the dispensation commences, only after this partial length of stroke has been covered.

Consequently, a complete return stroke is sufficient in order to nevertheless reproducibly dispense the quantity of liquid defined by the construction of the pump device during the next activation of the pump.

The dispensing head preferably has an inlet valve which is designed as a slide valve. This slide valve includes a valve duct which is preferably provided so as to be stationary on the base unit, and a valve slide which is preferably provided so as to be stationary on the dispensing unit and during dispensing moves into the valve duct as intended and, conjointly with an internal side of the valve duct, is designed for circumferential sealing. The delayed dispensation described above and the consistently uniform metered quantity can be particularly well implemented by such a valve. During activation, the pump chamber is isolated in relation to the liquid reservoir in that intermediate position in which the valve slide comes to bear circumferentially in the valve duct.

The outlet valve of the dispensing head preferably opens in a pressure-controlled manner, so that is opens under positive pressure in the pump chamber. The outlet valve is preferably designed as a "tip seal" valve which seals directly on the dispensing opening in such a way that the ingress of bacteria into the dispensing head is effectively prevented. This "tip seal" valve is preferably the only outlet valve. However, designs in which the dispending head has a first outlet valve which directly adjoins the pump chamber, and a second outlet valve which is downstream of the first outlet valve and is designed as a "tip seal" valve as described and is disposed directly on the dispensing opening, are also comprised.

The preferably only one outlet valve, as a valve which opens as a function of pressure, includes a valve body which is pushed to a closing position by a valve spring. This valve spring is preferably designed as a plastics-material spring in order to enable the uniform recycling of the dispensing head. The valve spring can likewise be designed as a bellows spring. However, because the valve spring of the outlet valve does not require a large spring travel, other designs are considered advantageous, in particular a design in which the valve spring is formed by a tubular spring body which by means of openings that penetrate the tubular body permits an elastic axial shortening. The openings are preferably formed in the shape of slots that are incorporated transversely to the compression direction.

The outlet valve is preferably designed in such a manner that a maximum pressure is required for opening at the beginning of an opening movement, wherein the outlet valve after opening can be kept open with a liquid pressure that is reduced in comparison to the maximum pressure. Therefore, the outlet valve in terms of construction is preferably designed in such a way that it at first does not open under increasing pressure. In this phase, a pressure level which after opening would be capable of keeping the valve open is not sufficient for opening the valve. This behavior is preferably achieved in that the valve body and a contact face of the dispensing unit bear on one another in the closed state of the outlet valve, and counteract opening due to the static friction prevailing therebetween. The static friction is only overcome once a sufficiently high pressure has been achieved, and the outlet valve opens abruptly. This opening characteristic prevents that the valve during opening at first only opens a tight outlet slot which compromises the dispensing characteristic.

The valve spring and the valve body of the outlet valve are preferably formed by an integral plastics-material part in order to achieve assembling of the dispensing head. Said valve spring and said valve body are in particular preferably composed of a polyolefin plastics material, in particular of polyethylene.

In order to prevent negative pressure from building up in the liquid reservoir as the dispensation of liquid from the liquid reservoir progresses, the dispensing head preferably provides a venting path along which compensation air from a surrounding atmosphere can flow into the liquid reservoir. The venting path herein then in particular lead through a venting chamber which is externally surrounded by the restoring spring in the form of a bellows spring. A venting opening which has an available cross section of at least 1 $mm^2$, in particular preferably of at least 5 $mm^2$, is preferably provided in the bellows spring, so that air from the outside can flow in there. This can in particular be a clearance on the end of the bellows body. However, it can also be expedient to impede the ingress of air into the venting chamber, or in the case of another profile of the venting path, to fully suppress said ingress of air, so that the restoring spring surrounds an air spring chamber within which air is contained, which air is compressed when the dispensing unit is displaced toward the base unit. In this instance, this air acts as an additional restoring spring.

In order to reduce the tendency of the liquid in the liquid reservoir to make its way to the outside by way of the venting path, the venting path at least in portions can be formed by a capillary duct which can be provided upstream or downstream of the venting chamber. If the capillary duct is provided upstream of the venting chamber in terms of an inflow direction, the capillary duct is preferably at least partially delimited by the bellows spring.

The venting duct mentioned can additionally have a filter unit which is preferably provided downstream of the venting chamber in terms of the inflow direction of the air, and which prevents or reduces the ingress of bacteria.

In a preferred design, the dispensing head is provided as a dispensing head for nasal application. For this purpose, the applicator housing, at least in a distal region, has an elongate shape which tapers toward a distal end. A finger rest, in particular an encircling finger rest, or a finger rest with two tabs for bearing the index finger and the middle finger, as has already been described above, for activation is preferably provided laterally on the applicator housing. In such a nasal applicator, a dispensing direction of the dispensing opening is preferably aligned so as to be parallel to the displacement direction of the dispensing unit relative to the base unit.

Another preferred construction mode is provided in particular for the topical application of liquids. Such a dispensing head can have a laterally disposed dispensing opening. A dispensing direction of the dispensing opening, conjointly with the displacement direction of the dispensing unit relative to the base unit, in this case encloses an angle>0°, preferably an angle between 5° and 100°, in particular an angle between 30° and 60°, or between 80° and 100°. In the case of such a dispensing head, depressing the dispensing unit is preferably performed by way of an activation face provided on the upper side of the dispensing head. In such a dispensing head it is preferably provided that the dispensing opening is provided on a port which protrudes laterally and protrudes outwardly beyond the external contour of the bellows spring.

The dispensing head, and in particular its dispensing opening, can be designed for different forms of application; the dispensing head is particularly preferably designed for dispensing a spray jet. For this purpose, said dispensing head can have a vortex chamber by way of which the exiting liquid is provided with a spin prior to exiting, said spin leading to a conical spray jet when exiting. Alternatively, the dispensing head can also have a plurality of fine nozzle openings for generating a spray jet, in particular a nozzle plate in which these nozzle openings are provided.

The design as a droplet dispenser with a droplet-forming face downstream of the dispensing opening for dispensing discrete single droplets, and the design as a dispenser for dispensing a non-atomized jet, are also possible.

As already mentioned above, the dispensing head and the entire dispenser are preferably designed with a view to permitting easy recycling.

The dispensing head, or the liquid dispenser, respectively, is preferably composed of polyolefin plastics material to an extent of at least 90%, preferably at least 95%, particularly preferably 99%. In particular, the dispenser can be largely or almost completely composed of polyethylene.

The liquid dispenser according to the invention has a dispensing head of the type described, and a liquid reservoir which is releasably or fixedly, or optionally even integrally, connected to the base unit. The liquid reservoir is preferably made of HDPE.

The liquid dispenser is usually delivered by the manufacturer to a filling company with an empty liquid reservoir, said filling company filling the latter with a liquid, in particular a pharmaceutical or cosmetic liquid. In the case of a pharmaceutical liquid, the latter is preferably provided for nasal application, oral application or topical application.

A pharmaceutical liquid is preferably filled into the liquid dispenser, wherein this is understood to mean in particular also saline aqueous solutions for application into the respiratory tracts of a patient. Aqueous solutions in the form of a Ringer's solution are also comprised, as are buffered solutions or aqueous solutions with at least one of the additives carbohydrates, etheric oils, menthol and plant extracts, as well as aqueous solutions containing vitamins, trace elements, manganese or zinc, or cinnamon oil, tea tree oil, sage oil, thyme oil, lemon balm oil.

The pharmaceutical liquid can in particular also be a liquid for nasal dispensation with a decongesting action, in particular a liquid with an imidazoline constituent such as, for example, oxymetazoline.

Apart from the dispensing head and the liquid dispenser as a whole, the invention also relates to a method for producing two types of dispensing heads. The method serves the purpose of enabling a particularly cost-effective production of the two types of dispensing heads in that many identical parts are used.

The dispensing heads of the first type include an external bellows spring as a restoring spring. These are preferably dispensing heads of the type described above.

The dispensing heads of the second type do not have any external bellows spring of plastics material but rather an internal coil spring, in particular a metallic coil spring. Such a coil spring is not provided in the first type.

The dispensing heads of both types have a base unit of identical construction for attaching to a liquid reservoir, and an applicator housing of identical construction, which as part of a dispensing unit is displaceable relative to the base unit and is penetrated by a dispensing opening. Apart from the spring used, the dispensing unit and the base unit of both types of dispensing heads additionally preferably differ from one another at most in terms of different finger rests, while all other components are identical.

The base unit and the applicator housing conjointly surround a spring receptacle space, thus a space in which the metallic coil spring, particularly preferably having a cylindrical basic shape in the case of the dispensing head of the second type, is received. The spring receptacle space at the end is preferably delimited in each case by annular contact faces on the base unit and on the dispensing unit, wherein the contact faces preferably on the inside and/or outside are flanked by guide spaces so as to hold the coil spring in position.

This spring receptacle space is also provided in dispensing heads of the first type. However, said spring receptacle space remains empty because the restoring action is caused by the external bellows spring. A metallic coil spring is inserted here only in dispensing heads of the second type.

Instead, in the dispensing heads of the first type the external plastics-material spring is attached, preferably by attaching a finger rest to which the bellows spring has already been previously fastened, or to which the bellows spring is integrally attached.

BRIEF DESCRIPTION OF THE DRAWINGS

Further advantages and aspects of the invention are derived from the claims and from the description hereunder of preferred exemplary embodiments of the invention which are explained hereunder by means of the figures.

DETAILED DESCRIPTION OF THE EXEMPLARY EMBODIMENTS

Figure 11:
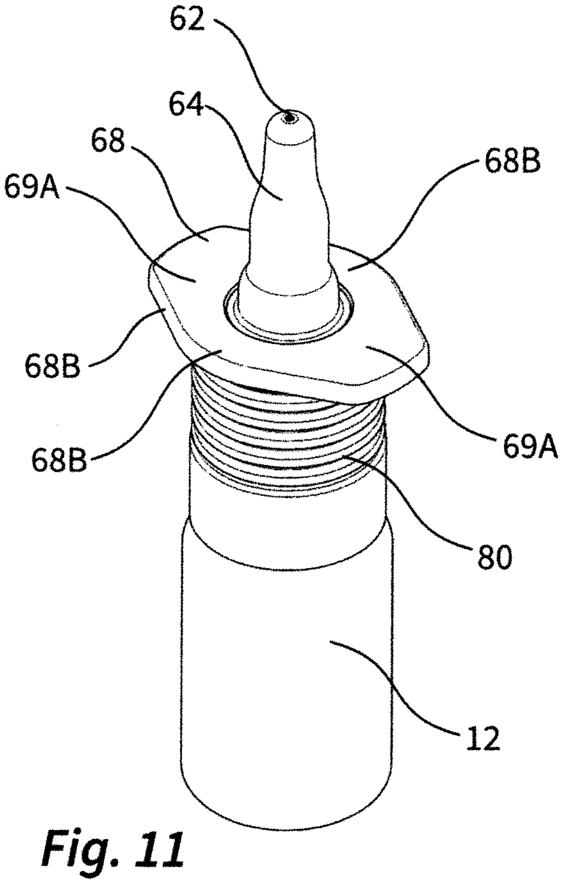
Figure 12:
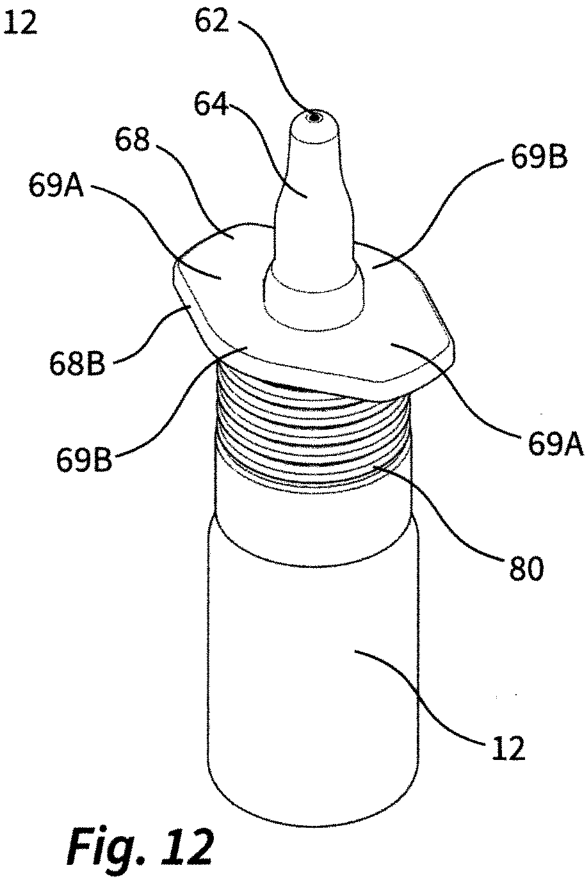

FIGS. 11 and 12 are perspective views of further embodiments of a liquid dispenser according to the invention, each featuring a non-circular finger rest.

Figure 1:
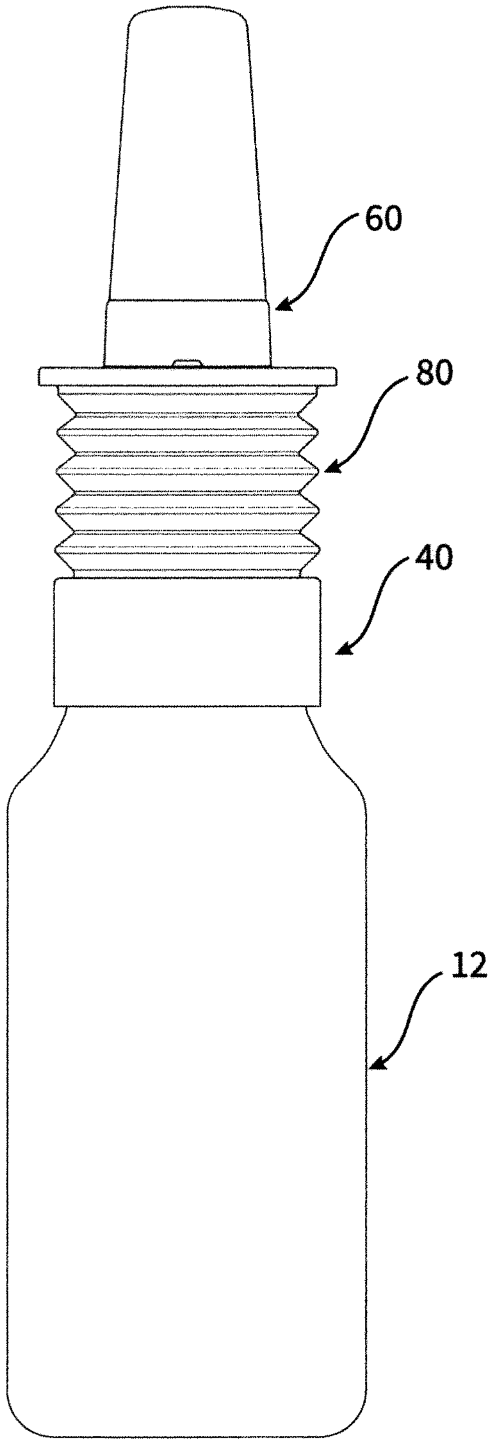
FIGS. 1 to 5 and 6A show a first exemplary embodiment of a liquid dispenser according to the invention, or the dispensing head of the latter, respectively.
Figure 2:
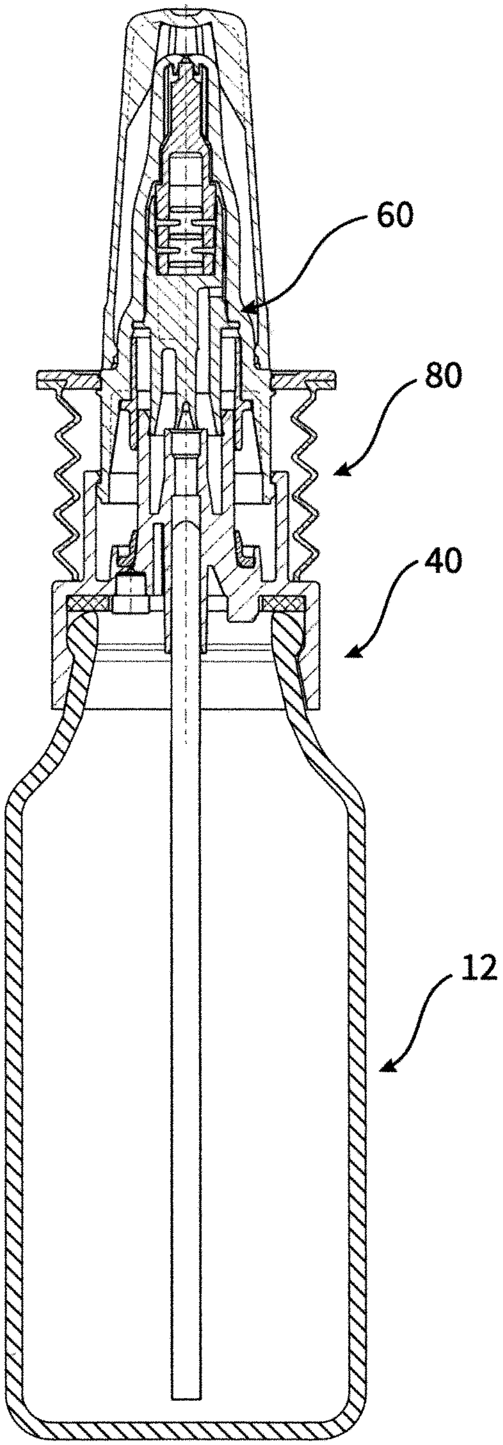
Figure 3A:
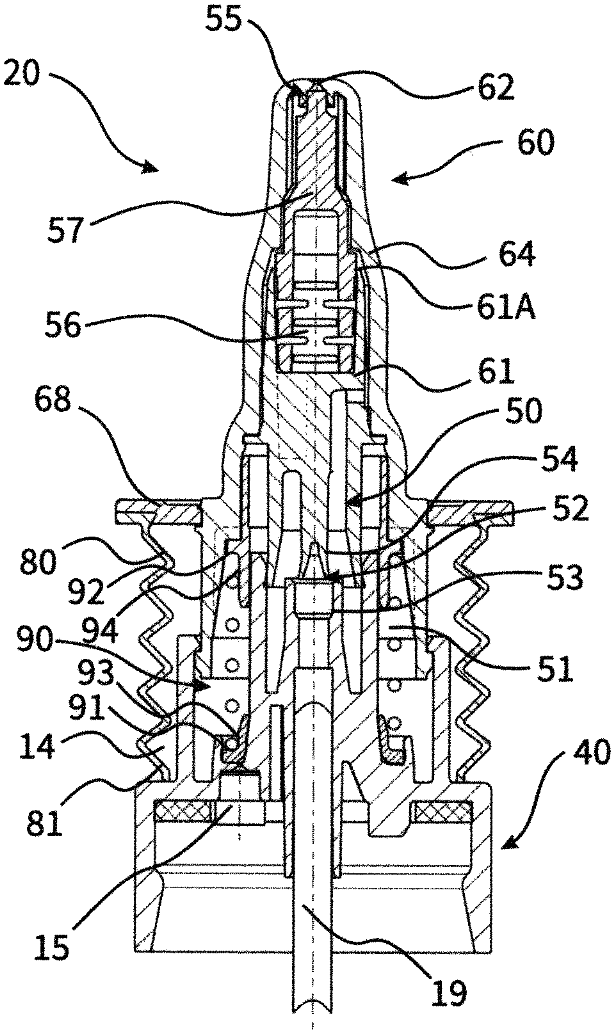
Figure 3B:
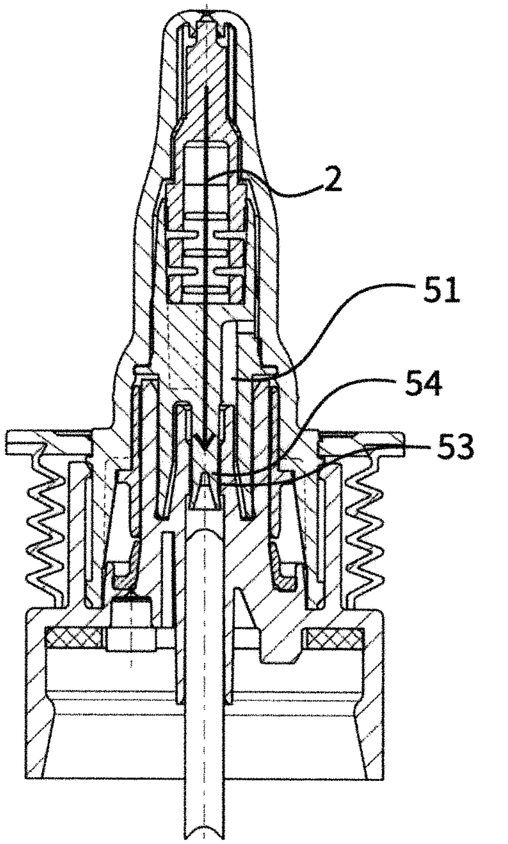

FIGS. 1 and 2 show the first exemplary embodiment of a liquid dispenser according to the invention in a sectional view and a non-sectional view. FIGS. 3A to 5 show the dispensing head 20 of this liquid dispenser 10, wherein the non-activated and the activated state are illustrated in FIGS. 3A and 3B.

The liquid dispenser 10 includes a liquid reservoir 12 in the form of a plastics-material bottle made of HDPE and having a circular cylindrical casing wall, and a dispensing head 20 which is fastened to the bottle neck of the liquid dispenser. In turn, the dispensing head 20 includes two main components which are mutually displaceable along a pumping direction 2, specifically a base unit 40 which is attached to the bottle neck of the liquid reservoir 12, and a dispensing unit 60 which is connected relative to the base unit 40 along the pumping direction 2.

A dispensing opening 62 by way of which liquid from the liquid reservoir 12 can be dispensed is provided on the distal end of the dispensing unit 60.

The dispensing head 20 for conveying the liquid from the liquid reservoir 12 to the dispensing opening 62 has a pump device 50. This pump devices 50 includes a pump chamber 51 which by way of an inlet duct is connected to an inlet valve 52 and to a riser 19 which protrudes into the liquid reservoir 12. The pump chamber 51 extends up to an outlet valve 55 which is disposed directly upstream of the dispensing opening 62.

The inlet valve 52 is designed as a slide valve. Said inlet valve 52 has a stepped valve duct 53 on the base unit 40, as well as a valve slide 54 on the dispensing unit 60, said valve slide 54 moving into said valve duct 53. When the dispensing unit 60 is depressed, as is highlighted by the transition from FIG. 3A to FIG. 3B, the valve slide 54 moves into the valve duct 53 and isolates the pump chamber 51 in relation to the liquid reservoir 12 as soon as the valve slide 54 reaches a tapered part of the valve duct 53. As from this point in time, liquid can no longer make its way from the pump chamber 51 back into the liquid reservoir 12, so that the continued depressing of the dispensing unit 60 causes a pressure increase in the isolated pump chamber 51.

The outlet valve 55 is designed as a tip-seal valve. This means that it closes directly in front of the dispensing opening 62. Said outlet valve 55 includes a valve body 57 and a valve spring 56, wherein the valve body 57 and the valve spring 56 are designed as an integral component, and by way of the end of the valve spring 56 are inserted into a clearance of an internal component 61 of the dispensing unit 60. The valve spring 56 is formed by a tubular spring body in which horizontal slots are provided in order to enable axial compression. The valve body 57 protrudes through a vortex chamber up to the dispensing opening 62, and closes the latter in a resting state.

An increase in pressure in the pump chamber 51 causes the valve body 57 to be impinged with a downward force which is suitable for displacing the valve body 57 in such a way that the outlet valve 55 is opened, and liquid can exit through the dispensing opening 62. Due to the vortex chamber, which is disposed upstream of the dispensing opening 62, the liquid exits in the form of a spray jet.

The integral component, which forms the valve body 57 and the valve spring 56, is guided externally by a sliding edge 61A of the internal component 61. In the event of a closed outlet valve, this sliding edge 61A causes static friction which has the effect that the outlet valve 55 does not immediately open when the pressure increases, but opens only with a slight delay yet abruptly. It is guaranteed as a result that the valve body 57 during dispensing is directly sufficiently spaced apart from the dispensing opening 62 in order to achieve an intended dispensation.

Depressing the dispensing unit 60 is performed by way of a finger rest 68 which in the exemplary embodiment of FIGS. 1 to 5 is attached externally to the applicator housing 64 by means of a latching connection. The user usually places his/her index finger and his/her middle finger on this finger rest 68, so as to depress the dispensing unit 60 relative to the base unit 40 by way of said finger rest 68.

In the absence of this activation force the dispensing unit 60 returns to its initial position illustrated in FIG. 3A. This takes place under the effect of a plastics-material restoring spring 80 which is designed in the manner of a bellows spring. This plastics-material restoring spring 80 is provided externally on the dispensing head 20 and encases the upper end of the base unit 40 and the lower end of the dispensing unit 60.

The design of the dispensing head with the plastics-material restoring spring 80 allows the entire dispensing head 20 to be made of plastics material. Since the plastics-material restoring spring 80 as well as the valve spring 56 are made of plastics material, the use of metallic coil springs can be dispensed with. All components, or at least 90% of the dispensing head 20 by weight, are preferably produced from polyolefin plastics materials, in particular from different varieties of polyethylene.

As can be seen by means of FIG. 3A, the dispensing head 20 includes a spring receptacle space 90 which is provided for receiving a metallic coil spring, but in the configuration of the dispenser according to FIGS. 1 to 5 is free of any such metallic restoring spring. This spring receptacle space 90 is delimited at its ends by a first annular contact face 91 on the base unit 40 and a second annular contact face 92 on the dispensing unit 60. However, this spring receptacle space 90 allows a dispensing head 20, which is similar to the one described here and does not include an external plastics-material restoring spring 80 but instead an internal metallic coil spring, to be made available while using many identical parts. This will also still be shown hereunder.

While the use of a plastics-material restoring spring 80 offers significant advantages with a view to recycling, a restoring action which is equally strong and relaxation-free as that of a metallic coil spring is not usually guaranteed by said plastics-material restoring spring 80. The choice of the design of the pump device 50 takes this into account. Because the valve slide 54 described has at first to be displaced downward a few millimeters in the course of activation before said valve slide 54 closes the inlet valve 52, it is not that important in a dispenser of the type illustrated that the plastics-material restoring spring 80 actually pushes the dispensing unit 60 all the way to the uppermost terminal position of FIG. 3A. Even when a plastics-material restoring spring 80 which is partially relaxed due to a long storage period, for example, is used, this plastics-material restoring spring 80 is usually sufficient for pushing the valve slide 54 conjointly with the dispensing unit 60 so far upward that the valve slide 54 is extracted from the tapered part of the valve duct 53. This is sufficient for orderly functioning of the pump device 50.

FIG. 3B highlights that, when depressing the dispensing unit 60, the valve slide 54 in its terminal position leaves the tapered part of the valve duct 53 again, so that the positive pressure in the pump chamber 51 is abruptly reduced at this moment, the dispensation thus ending. The dispensed quantity of the pump device 50 is determined solely by the length of the tapered part of the valve duct 53.

Figure 4:
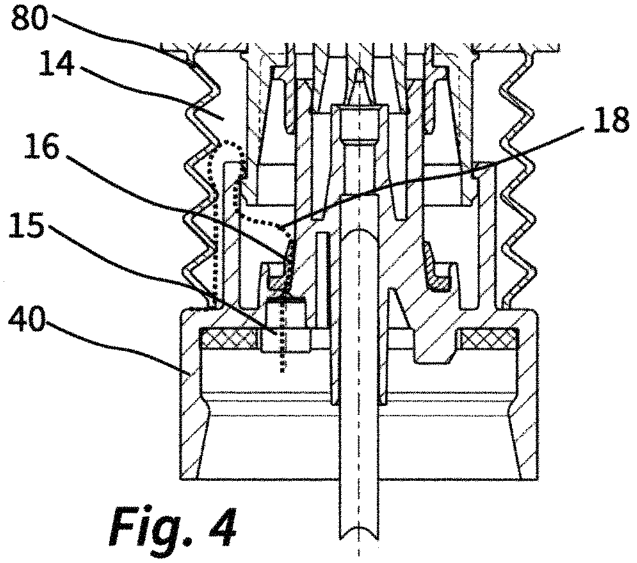

When the dispensing head 20 returns from the activated state of FIG. 3B to the non-activated state of FIG. 3A, liquid is induced into the pump chamber 51 through the riser 19. This results in negative pressure in the liquid reservoir 12, which is equalized by a venting duct. The corresponding venting path 18 is illustrated in FIG. 4. The venting path runs from the outside to the inside, first through a gap which is formed by the plastics-material restoring spring 80, designed as a bellows spring, conjointly with the housing of the base unit 40. The venting path 18 runs onward through a guide of the dispensing unit 60 and of the base unit 40 into a capillary duct 16, which is formed by the base body of the base unit 40 and a sleeve pushed thereon, up to a filter unit 15 in which the inflowing air is relieved of bacteria.

It is particularly relevant herein that the venting path 18 runs through a venting chamber 14 which is externally delimited by the plastics-material restoring spring 80, designed as a bellows spring. As described at the outset, the inflow of air takes place through a gap on the lower end of the plastics-material restoring spring 80. This here is a very narrow gap, so that the air, which is humidified by the liquid in the liquid reservoir 12, in the venting chamber 14 can escape into the environment only to a minor degree.

Figure 5:
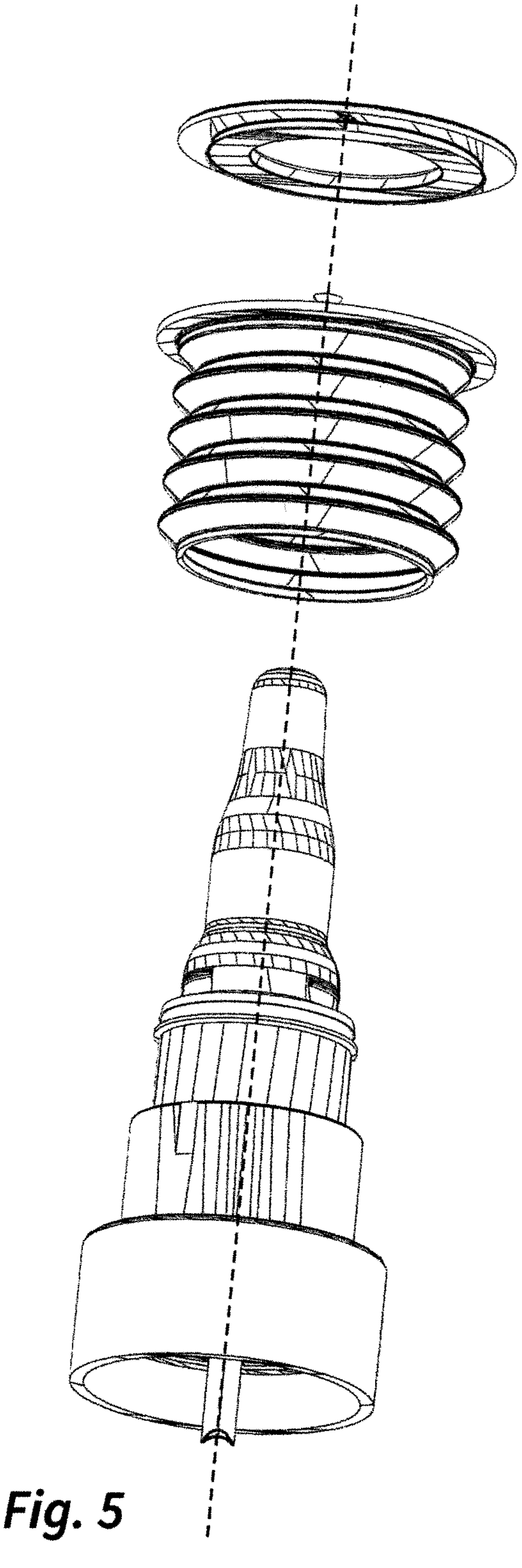

FIG. 5 shows the dispensing head 20 once again, wherein it is highlighted here that the dispensing head 20 as a whole can already have been assembled when the plastics-material restoring spring 80 as well as the finger rest 68 are finally assembled.

FIGS. 6A to 6D show different designs of the finger rest 68 and of the plastics-material restoring spring 80.

Figure 6A:
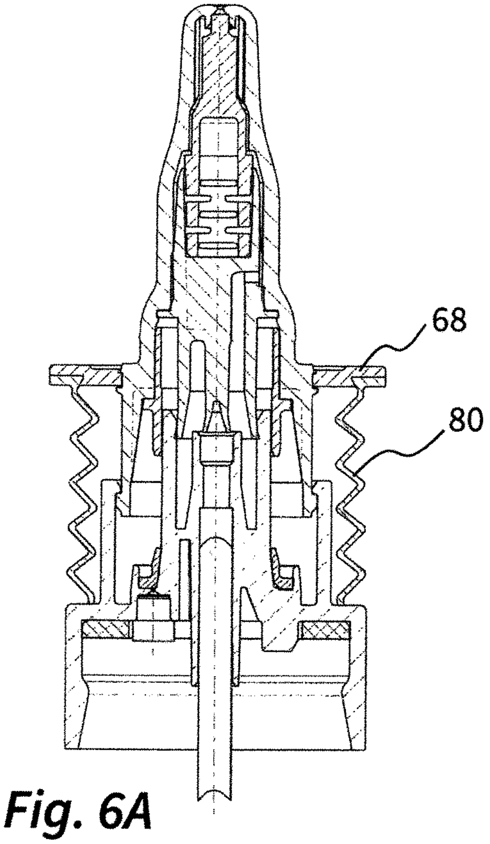

FIG. 6A shows the version already illustrated in the preceding figures. Here, the finger rest 68 and the plastics-material restoring spring 80 are implemented as one integral component which is produced by a bicomponent injection-molding process. This means that the bellows spring can be handled indirectly via the finger rest 68 and be attached to the base unit 40 and the dispensing unit 60 during assembling.

Figure 6B:
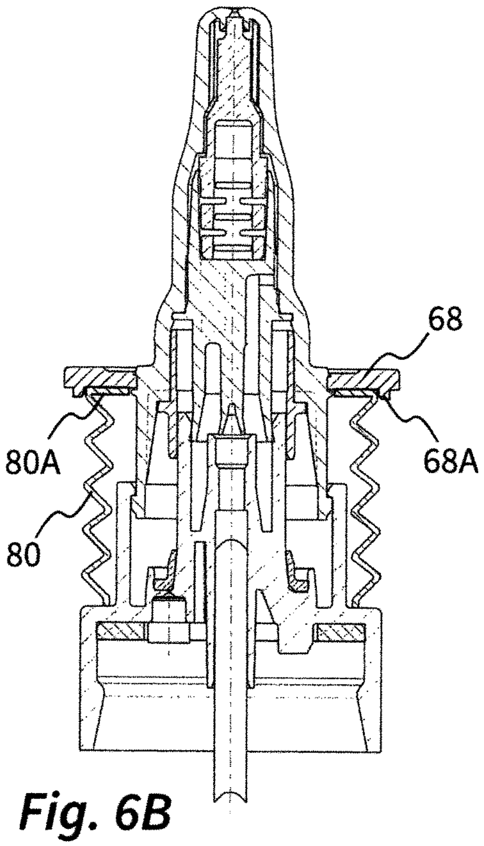
FIGS. 6B to 6D show structural alternatives to FIGS. 1 to 6A.

In the design according to FIG. 6B it is provided that the plastics-material restoring spring 80 and the finger rest 68 form separate components. The plastics-material restoring spring 80 on its upper end has an inward-pointing encircling collar 80A which has an internal diameter which is reduced in comparison to the pleats of the bellows. Such a collar 80A assists the demolding of the bellows during production. In the case of the illustration of FIG. 6B, the finger rest 68 is provided with an encircling centering periphery 68A which guarantees the positional stability of the plastics-material restoring spring 80. Because the collar 80A points inward up to the applicator housing 64 and thus causes centering in itself, such an additional centering feature is however not mandatory.

Figure 6C:
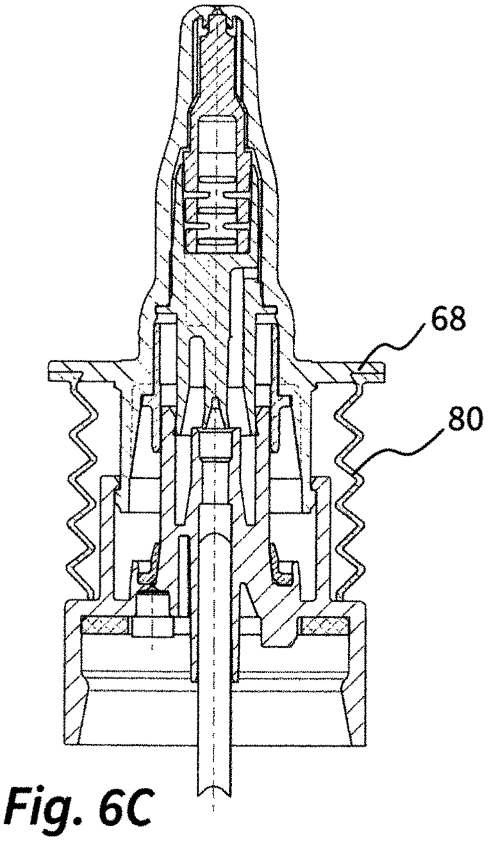

FIG. 6C shows a design in which the bellows is designed to be integral to the finger rest 68, as in FIG. 6A. The peculiarity here is that the finger rest 68 is designed to be integral to the applicator housing 64. This means that during assembling the finger rest 68 and the plastics-material restoring spring 80 are also assembled as a result of the dispensing unit 60 being attached to the base unit 40.

Figure 6D:
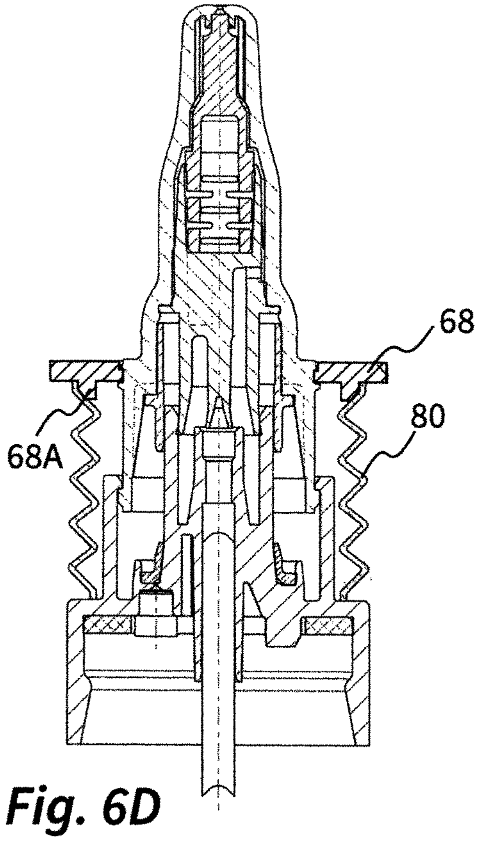

The design of FIG. 6D is similar to that of FIG. 6B. Here too, the bellows is designed as a separate component. Here too, the finger rest 68 has a centering ring 68A which in this case however centers the plastics-material restoring spring 80 from the inside.

Figure 7:
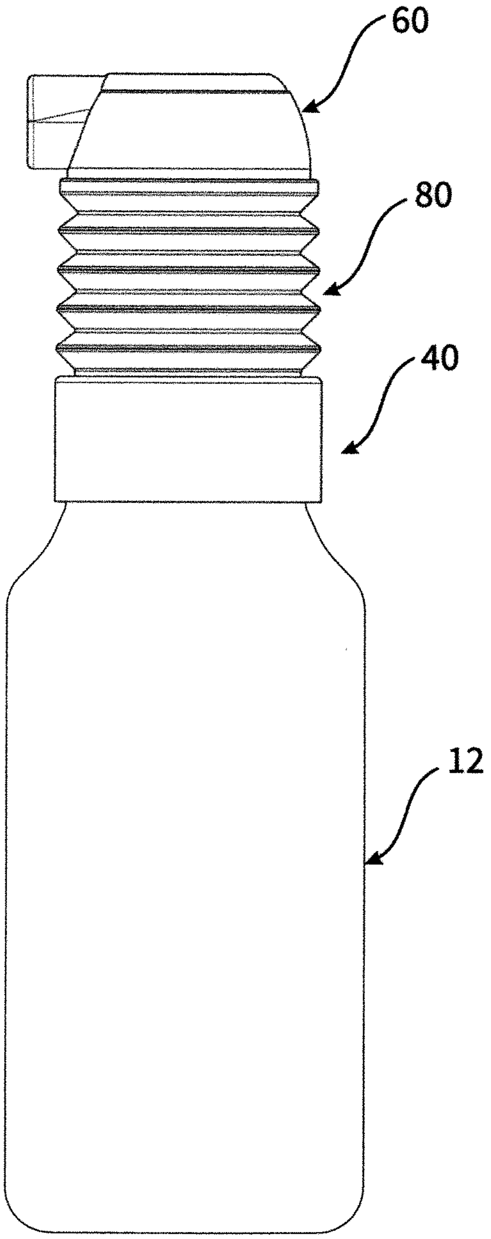
FIGS. 7 to 9B show a second exemplary embodiment of a liquid dispenser according to the invention, or of the dispensing head of the latter, respectively.
Figure 8:
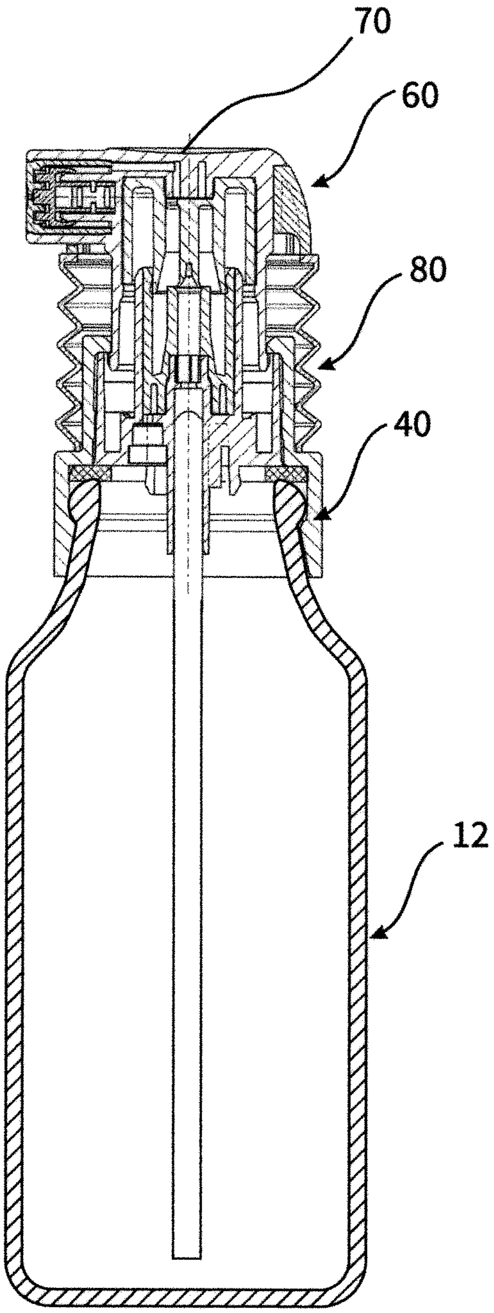
Figure 9A:
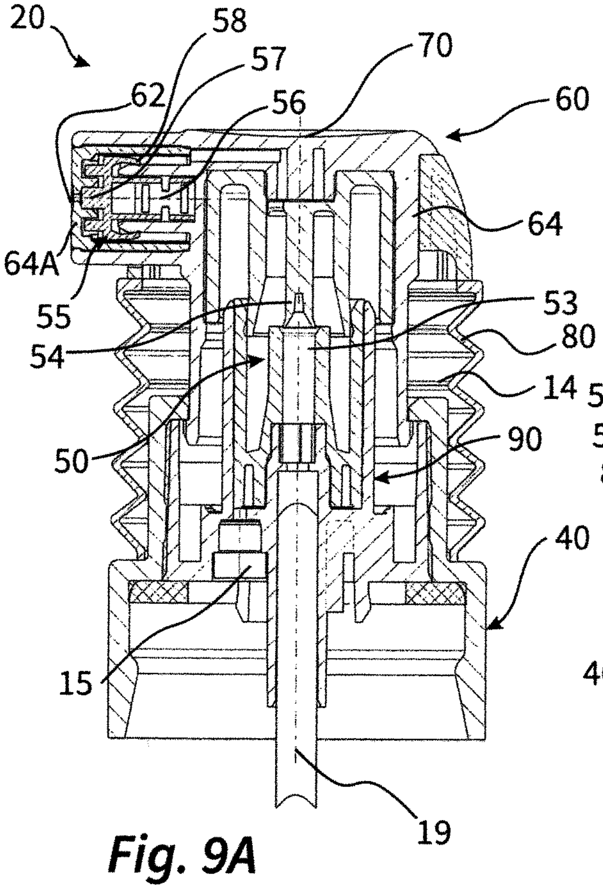
Figure 9B:
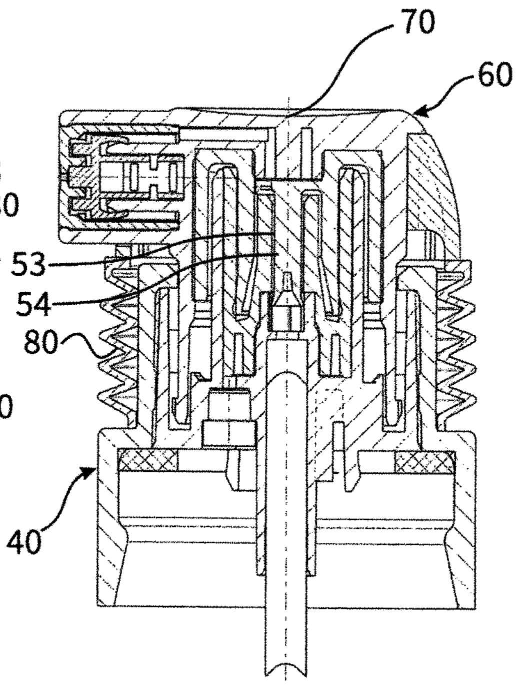

FIGS. 7 to 9B show a liquid dispenser 10 of a different type, which differs from the design of FIGS. 1 to 6 in terms of the fundamental shaping. FIGS. 7 and 8 show the liquid dispenser 10 in a sectional view and a non-sectional view. FIGS. 9A and 9B show the dispensing head 20 of this liquid dispenser 10 in the non-activated and activated state.

The liquid dispenser 10 illustrated here is provided for topical application. Said liquid dispenser 10 serves the purpose of applying liquid to the skin of a patient.

For this reason, the dispensing opening 62 in this design is also provided laterally on the dispensing head 20. The dispensing direction, conjointly with an activation direction 2 in which the dispensing unit 60 is displaceable relative to the base unit 40, encloses an angle of 90°. While the pump chamber and the inlet valve are designed so as to be largely identical to the design of FIGS. 1 to 6, the outlet valve 55, like the dispensing opening 62, is provided laterally in this design. Moreover, it is provided that sealing between the valve body 57 and the dispensing unit 60 is performed by sealing lips 58 which are provided on the valve body 57. The valve body 57 and the valve spring 56 are disposed in a receptacle space which is shut off by a closure part 64A of the applicator housing 64.

Activation takes place by means of an activation face 70 which is provided on the upper side of the dispensing unit 60.

Figure 10:
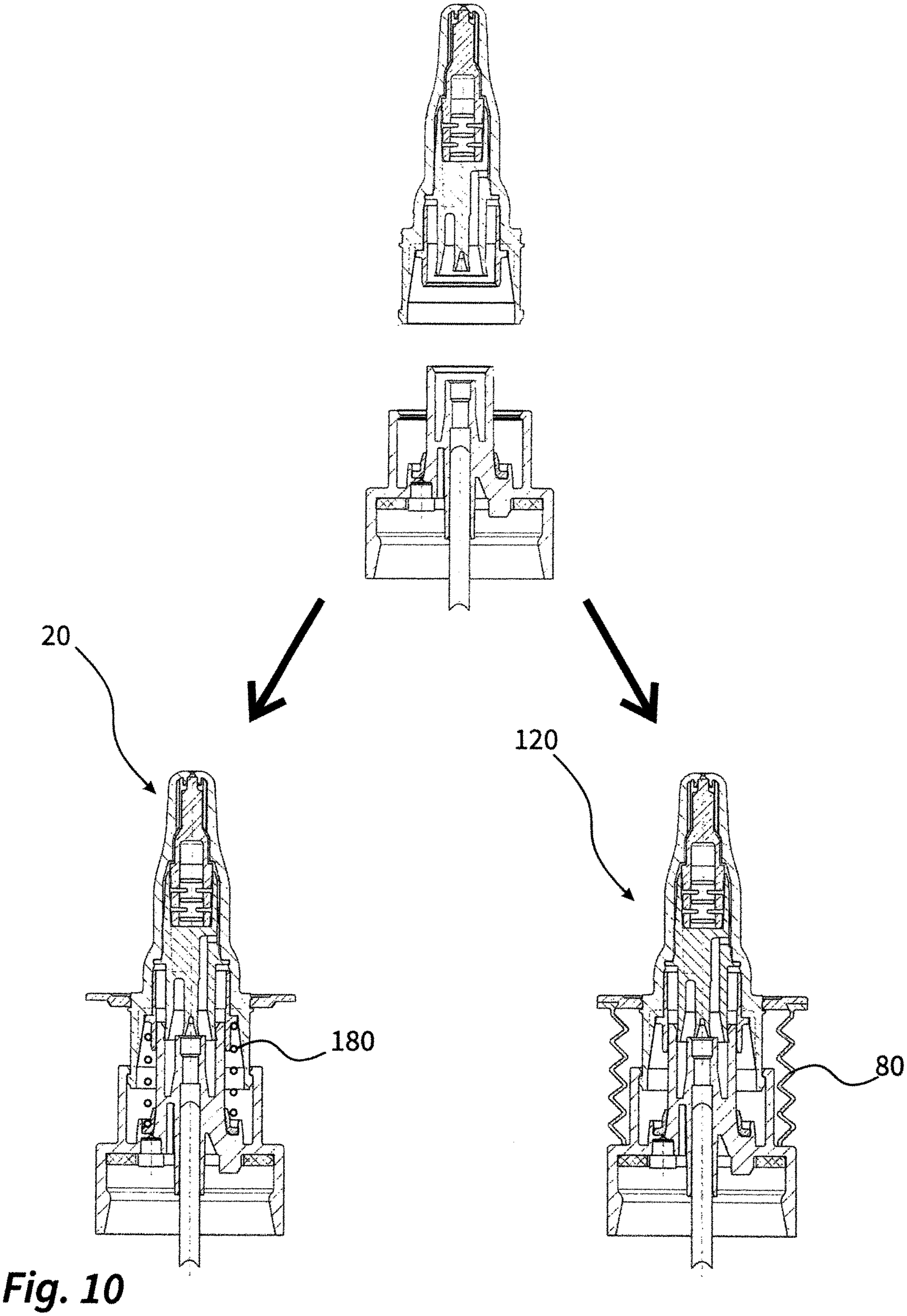
FIG. 10 highlights how different types of dispensing heads are generated based on components of largely identical construction.

It is yet again highlighted by means of FIG. 10 how the dispensing head 20 illustrated, in particular that of FIGS. 1 to 5, can be the basis for a product range with different dispensing heads. To this end, FIG. 10 in the upper half of the figure shows the two relevant sub-units of the dispensing head 20, i.e. the base unit 40 as well as the dispensing unit 60, wherein the dispensing unit 60 is not yet provided with a finger rest 68.

These two sub-units 40, 60 are identical for two designs of the dispensing head 20, specifically for the variant illustrated on the left in the figure, having an internal metallic coil spring as the restoring spring 180, as well as for the variant on the right-hand side in FIG. 10, which corresponds to the variant of FIGS. 1 to 5.

This ability to reuse the modules shown at the top in FIG. 10 leads to reduced costs. Furthermore, this also facilitates the logistics because the modules at the top in FIG. 11 can be stored in a prefabricated state and be used for dispensing heads with metallic coil springs and for advantageously recyclable dispensing heads with an external bellows spring, depending on the order situation.

FIGS. 11 and 12 show two designs of a liquid dispenser, which in terms of their internal construction mode are substantially identical to that of FIGS. 1 to 6. The peculiarity here lies in the shaping of the finger rest 68. The finger rest 68 does not have a round external contour but an approximately elliptic external contour 68B which protrudes radially beyond the circular cylindrical casing wall of the liquid reservoir 12. Two contact faces 69A on both sides of the applicator 64 point toward the outside and protrude beyond the liquid reservoir 12 in the radial direction. They serve for resting two fingers, in particular an index finger and a middle finger. Connecting pieces 69B which do not protrude as far radially are provided between the activation faces 69A, wherein these connecting pieces 69B are optional in the case of the design of FIG. 12.

The construction mode of FIGS. 11 and 12, having the two tab-like activation faces 69A, leads to the liquid dispenser as a whole losing its ability to roll. This may simplify the recycling process, because the liquid dispensers cannot fall off conveyor belts and can in particular be removed from a transport belt in a reproducible manner by targeted air pulses. In contrast, such handling is more difficult in the case of liquid dispensers with a rolling capability.

The designs of FIGS. 11 and 12 differ from one another in that, in the case of the design of FIG. 11, the finger rest 68 is formed by a component which is separate from the applicator 68, preferably by a component which is designed to be integral to the spring 80. In contrast, in the design of FIG. 12, an integral connection is provided between the applicator 68 and the finger rest 68, similar to FIG. 6C.

The invention claimed is:

1. A dispensing head for pharmaceutical or cosmetic liquids, comprising:

a base unit configured for attaching to a liquid reservoir;

a dispensing unit, the dispensing unit comprising:

an applicator housing penetrated by a dispensing opening; and a finger rest for applying a force on the dispensing unit in a direction of the base unit, the finger rest being annular and externally surrounding the applicator housing;

a restoring spring, the restoring spring being configured as a plastics-material spring, the dispensing unit being displaceable, counter to a force of the restoring spring, relative to the base unit, the restoring spring, proximal to the dispensing unit, acting on an underside of the finger rest; and a pump device, the pump device being activatable by movement of the dispensing unit relative to the base unit, and in response to an activation the pump device is configured to convey liquid from the liquid reservoir to the dispensing opening.

2. The dispensing head as claimed in claim 1, wherein the dispensing unit has an external side and the base unit has external faces, the restoring spring being attached to the external side of the dispensing unit and encasing the external faces of the base unit and portions of the external side of the dispensing unit.

3. The dispensing head as claimed in claim 1, wherein the restoring spring and the finger rest are fixedly connected to one another such that the restoring spring and the finger rest can be conjointly handled when assembling the dispenser.

4. The dispensing head as claimed in claim 1, wherein the restoring spring has a force-introduction face, the finger rest and the restoring spring are configured as separate components and the finger rest includes a centering geometry guiding the force-introduction face of the restoring spring from an inside and/or an outside.

5. The dispensing head as claimed in claim 1, wherein the finger rest is configured as a component separate from the applicator housing and is fastened to an external side of the applicator housing.

6. The dispensing head as claimed in claim 1, wherein the finger rest is configured to be integral with the applicator housing.

7. The dispensing head as claimed in claim 1, wherein the finger rest externally has a non-circular shape and has two pad regions for two fingers disposed on opposite sides of the applicator housing.

8. The dispensing head as claimed in claim 1, wherein the dispensing unit is displaceable relative to the base unit over a total length of stroke between a non-activated initial position and an activated terminal position, and the pump device is configured and/or coupled to the dispensing unit such that, proceeding from the non-activated initial position, a displacement of the dispensing unit in a direction of the activated terminal position does not cause any liquid dispensation over a partial length of stroke, and the partial length of stroke is at least 3% of a total length of stroke.

9. The dispensing head as claimed in claim 1, wherein the pump device has an inlet valve configured as a slide valve, and the inlet valve includes a valve duct and a valve slide, the valve slide, for circumferential sealing, being formed conjointly with an internal side of the valve duct.

10. The dispensing head as claimed in claim 1, wherein:

the pump device has a pump chamber and an outlet valve, the outlet valve opening or closing as a function of a liquid pressure in the pump chamber;

the outlet valve includes a valve body pushed to a closing position by a valve spring; and the valve spring is configured as a plastics-material spring.

11. The dispensing head as claimed in claim 10, wherein the valve spring and the valve body are part of an integral component.

12. The dispensing head as claimed in claim 1, wherein:

a dispensing direction of the dispensing opening is aligned so as to be parallel to a displacement direction of the dispensing unit relative to the base unit; or a dispensing direction of the dispensing opening, conjointly with a displacement direction of the dispensing unit relative to the base unit, encloses an angle of >0.

13. The dispensing head as claimed in claim 1, wherein the restoring spring surrounds an air spring space containing air compressed when the dispensing unit is displaced relative to the base unit.

14. The dispensing head as claimed in claim 1, wherein the dispensing head is configured for nasal application, and the applicator housing has an elongate shape tapering toward a distal end, the dispensing opening being disposed on the distal end of said applicator housing.

15. The dispensing head as claimed in claim 1, including at least one of the following:

the dispensing head is configured as a spray head; and/or the restoring spring is separated from a liquid path from the liquid reservoir to the dispensing opening and is not in contact with liquid; and/or the dispensing head comprises polyolefin plastics materials to an extent of at least 90%; and/or the restoring spring comprises a thermoplastic elastomer; and/or the restoring spring comprises a plastics-material bellows spring having a last bellows segment disposed on the base unit and comprising a bellows segment tapering in a distal direction.

16. The dispensing head as claimed in claim 1, further comprising:

a spring receptacle space configured to receive a coil spring and disposed between the base unit and the dispensing unit; and annular contact faces are disposed on the base unit and the dispensing unit, the annular contact faces being delimited on an inside and/or an outside by guide faces.

17. The dispensing head as claimed in claim 1, wherein the restoring spring comprises a bellows spring.

18. The dispensing head according to claim 1, wherein the applicator housing has a terminal upper end and the finger rest is spaced from both the terminal upper end of the applicator housing and the base unit, and the restoring spring is disposed between the base unit and the finger rest and acts on the underside of the finger rest facing the base unit.

19. A dispensing head for pharmaceutical or cosmetic liquid, comprising:

a base unit configured for attaching to a liquid reservoir;

a dispensing unit having an applicator housing penetrated by a dispensing opening;

a restoring spring, the restoring spring being configured as a plastics-material spring, the dispensing unit being displaceable, counter to a force of the restoring spring, relative to the base unit;

a pump device, the pump device being activatable by movement of the dispensing unit relative to the base unit, and in response to an activation the pump device is configured to convey liquid from the liquid reservoir to the dispensing opening; and a rigid component fixedly attached to the dispensing unit or to the base unit and the restoring spring is only fixedly attached to the rigid component.

20. A dispensing head for pharmaceutical or cosmetic liquids, comprising:

a base unit configured for attaching to a liquid reservoir;

a dispensing unit having an applicator housing penetrated by a dispensing opening;

a restoring spring, the restoring spring being configured as a plastics-material spring, the dispensing unit being displaceable, counter to a force of the restoring spring, relative to the base unit;

a pump device, the pump device being activatable by movement of the dispensing unit relative to the base unit, and in response to an activation the pump device is configured to convey liquid from the liquid reservoir to the dispensing opening; and a venting path, wherein compensation air flows along the venting path from a surrounding atmosphere and into the liquid reservoir, and the venting path extends through a venting chamber externally surrounded by the restoring spring.

21. A liquid dispenser comprising:

a liquid reservoir; and a dispensing head, the dispensing head comprising:

a base unit attached to the liquid reservoir;

a dispensing unit, the dispensing unit comprising:

an applicator housing penetrated by a dispensing opening; and a finger rest for applying a force on the dispensing unit in a direction of the base unit the finger rest being annular and externally surrounding the applicator housing;

a restoring spring, the restoring spring being configured as a plastics-material spring, the dispensing unit being displaceable, counter to a force of the restoring spring, relative to the base unit, the restoring spring, proximal to the dispensing unit, acting on an underside of the finger rest; and a pump device, the pump device being activatable by movement of the dispensing unit relative to the base unit and, in response to an activation conveys liquid from the liquid reservoir to the dispensing opening.

22. The liquid dispenser as claimed in claim 21, wherein:

the liquid reservoir comprises a circular cylindrical casing wall; and the finger rest has a non-circular shape and an external contour protruding radially beyond the circular cylindrical casing wall of the liquid reservoir at least in portions.

23. The liquid dispenser as claimed in claim 21, wherein the liquid dispenser comprises polyolefin plastics materials to an extent of at least 90%.

24. The liquid liquid dispenser according to claim 21, wherein the applicator housing has a terminal upper end and the finger rest is spaced from both the terminal upper end of the applicator housing and the base unit, and the restoring spring is disposed between the base unit and the finger rest and acts on the underside of the finger rest facing the base unit.

25. A method for producing two types of dispensing heads, comprising:

producing dispensing heads of a first type each including an external bellows spring as a restoring spring;

producing dispensing heads of a second type, each including an internal coil spring as a restoring spring;

providing the dispensing heads of the first and the second types with a base unit of identical construction for attaching to a liquid reservoir, and an applicator housing of identical construction, the applicator housing being displaceable relative to the base unit and being penetrated by a dispensing opening;

in the dispensing heads of the first type, externally attaching the restoring spring such that said restoring spring encases the applicator housing and the base unit at least in portions; and in the dispensing heads of the second type, incorporating the restoring spring in a spring receptacle space externally surrounded by the base unit and the applicator housing, the spring receptacle space at the end being delimited by internal annular contact faces of the base unit and the applicator housing.

* * * * *